United States Patent
Little, III et al.

(10) Patent No.: US 9,086,373 B2
(45) Date of Patent: Jul. 21, 2015

(54) METHOD AND SYSTEM FOR BLENDING FLUIDS

(71) Applicant: JP3 Measurement, LLC, Austin, TX (US)

(72) Inventors: Joseph Paul Little, III, Austin, TX (US); Matt Thomas, Austin, TX (US)

(73) Assignee: JP3 Measurement, LLC, Austin, TX (US)

( * ) Notice: Subject to any disclaimer, the term of this patent is extended or adjusted under 35 U.S.C. 154(b) by 0 days.

(21) Appl. No.: 14/530,982

(22) Filed: Nov. 3, 2014

(65) Prior Publication Data

US 2015/0047712 A1    Feb. 19, 2015

Related U.S. Application Data

(63) Continuation-in-part of application No. 14/161,911, filed on Jan. 23, 2014, now Pat. No. 9,000,375, which is a continuation of application No. 13/720,598, filed on Dec. 19, 2012, now Pat. No. 8,686,364.

(60) Provisional application No. 61/702,151, filed on Sep. 17, 2012.

(51) Int. Cl.
| | |
|---|---|
| G01N 21/3504 | (2014.01) |
| G01N 21/35 | (2014.01) |
| G01N 21/85 | (2006.01) |
| G01N 33/28 | (2006.01) |
| G01J 3/02 | (2006.01) |
| G01J 3/28 | (2006.01) |
| G01J 3/45 | (2006.01) |
| G01N 21/359 | (2014.01) |
| G01J 3/433 | (2006.01) |
| F17D 3/01 | (2006.01) |
| G05D 11/13 | (2006.01) |
| G01J 3/10 | (2006.01) |

(52) U.S. Cl.
CPC .............. *G01N 21/3504* (2013.01); *F17D 3/01* (2013.01); *G01J 3/02* (2013.01); *G01J 3/0294* (2013.01); *G01J 3/28* (2013.01); *G01J 3/433* (2013.01); *G01N 21/35* (2013.01); *G01N 21/359* (2013.01); *G01N 21/85* (2013.01); *G01N 33/28* (2013.01); *G05D 11/132* (2013.01); *G01J 3/108* (2013.01); *G01N 2201/06113* (2013.01); *Y10T 137/0335* (2013.01); *Y10T 137/2506* (2013.01)

(58) Field of Classification Search
CPC ....... G01N 21/35; G01N 21/3504; G01J 3/02; G01J 3/0294
See application file for complete search history.

(56) References Cited

U.S. PATENT DOCUMENTS

| | | | | |
|---|---|---|---|---|
| 5,712,481 | A * | 1/1998 | Welch et al. | 250/339.12 |
| 5,717,209 | A * | 2/1998 | Bigman et al. | 250/339.12 |
| 5,723,338 | A * | 3/1998 | Rutledge et al. | 436/56 |
| 2003/0199649 | A1 * | 10/2003 | Orbison et al. | 526/123.1 |
| 2005/0099618 | A1 * | 5/2005 | DiFoggio et al. | 356/70 |
| 2013/0033702 | A1 * | 2/2013 | Tunheim et al. | 356/73 |

* cited by examiner

*Primary Examiner* — David Porta
*Assistant Examiner* — Mindy Vu
(74) *Attorney, Agent, or Firm* — DuBois, Bryant & Campbell LLP; William D. Wiese (57) ABSTRACT

Methods and systems for real time, in situ monitoring and blending of hydrocarbon fluids from multiple transmission lines feeding into a downstream line or vessel are described. The method and system include the scanning of the NIR range on fluids within each of at least two transmission lines. The spectroscopic optical data from the two scans is used to determine flow rates of the fluids from each transmission line to, for example, achieve a desired energy content, physical properties, or speciation in the blended fluid.

24 Claims, 5 Drawing Sheets

METHOD AND SYSTEM FOR BLENDING FLUIDS

CROSS-REFERENCE TO RELATED APPLICATIONS

This non-provisional application is a continuation of U.S. patent application Ser. No. 14/161,911 filed Jan. 23, 2013 in the names of Joseph Paul Little, III, Matt Thomas, and Jie Zhu entitled "METHOD AND SYSTEM FOR DETERMINING ENERGY CONTENT AND DETECTING CONTAMINANTS IN A FLUID STREAM." U.S. patent application Ser. No. 14/161,911 is a Continuation of U.S. patent application Ser. No. 13/720,598 filed Dec. 19, 2012, now U.S. Pat. No. 8,686,364 issued Apr. 1, 2014 in the names of Joseph Paul Little, III and Matt Thomas entitled "METHOD AND SYSTEM FOR DETERMINING ENERGY CONTENT AND DETECTING CONTAMINANTS IN A FLUID STREAM," which claims priority based upon prior U.S. Provisional Patent Application Ser. No. 61/702,151 filed Sep. 17, 2012 in the names of Joseph Paul Little, III and Matt Thomas entitled "TRACE H2S DETECTION WITH NEAR IR SPECTROSCOPY IN NATURAL GAS STREAM UNDER PRESSURE UTILIZING A SCANNING LIGHT SOURCE," the disclosures of which are incorporated herein in their entirety by reference as if fully set forth herein.

BACKGROUND OF THE INVENTION

Crude oil from individual oil wells is transported through flow lines to individual vessels generally located at or near the well site. From there, the oil may undergo further separation, treating, heating, dehydrating, compressing, blending, pumping or other processing activities before being transported downstream, via truck, pipeline, rail car or other transportation method. It can enter into gathering lines to a point where it enters a common carrier pipeline and eventually arrives at the refinery. When custody of oil is transferred from one owner or processing point to another during this process, it is useful to know the composition and physical properties of the oil being transferred for a variety of reasons, including, but not limited to, the sale price of the crude, the desired final destination for refining, and the timing of the delivery, safety and material handling requirements for storage/transportation.

The current standard for assessing the "quality" of oil in the field is determining its relative density or API gravity, vapor pressure, water content, and basic solids and water content ("BS&W"). Upper limits are set on the BS&W content and vapor pressure; and, the pricing of the oil is generally related to the API gravity number. In the past, oil produced from conventionally drilled wells with certain API numbers would generally all have similar compositional values. However, this general correlation is increasingly being challenged. One of the biggest contributing factors challenging this historical assumption is new production from unconventional shale formations. This shale crude oil tends to be much lighter (higher API gravity number) and can vary significantly in composition from well to well, and even from within an individual well. The amount of time the crude is stored in a tank can also have an effect on the composition. As the crude sits, it becomes "weathered", meaning some of the lighter components have flashed off and been vented, flared, or injected into the gas phase pipeline leaving the production facility. The increasing and changing sources of production have also resulted in the comingling of various streams from different sources to generate oil with specific desired properties, resulting in much different hydrocarbon compositions of blended oil than previously seen.

It would be useful to know the constituent compositions of the oil entering the common carrier line from each gathering line in real time so that the composition of the oil in the common carrier line can be monitored and adjusted as desired to meet specifications such as those imposed by individual refineries. This would enable the prevention of practices such as "bar-bell-ing" where a specified API gravity number is obtained through the combination of light end hydrocarbons with much heavier "sludge" hydrocarbons without the highly desirable intermediates such as C7-C12. It would also allow for blending and marketing of very specific oil compositions to take place even upstream or midstream, well before selling to the refineries. Finally, it would allow the refineries to significantly increase their production efficiency and thus profit margins by monitoring incoming oil composition and paying more or less for specific blends, rather than just relying on API gravity numbers.

There is a need, therefore, for a method and system for determining the energy content, physical properties and the constituent composition of crude oil entering the common carrier lines or other transportation systems such as rail cars or trucks from each gathering line, or passing through custody transfer points, in real time so that the composition of the oil can be monitored and adjusted as desired.

SUMMARY OF THE INVENTION

Embodiments of the present invention include methods and systems for real time, in situ monitoring and blending of fluids from multiple transmission lines or other lines feeding into a downstream pipeline or vessel. The method and system include the scanning of the NIR range on fluids within each of at least two transmission lines. The scan ranges from approximately 1350 nm up through 1850 nm. The spectroscopic optical data from the scan is used to determine composition and other physical properties of the incoming fluid streams, which can then be used to alter flow rates from each line, thereby affecting the composition of the fluid downstream from the transmission lines.

Monitoring and adjusting the relative flows of fluids in transmission lines in real time can be used for a variety of purposes. For example, when the fluids in each transmission line have different energy contents or contaminant levels, embodiments of the present invention allow the flows to be monitored and altered to achieve a blended product with desired characteristics downstream from the transmission lines. In addition, embodiments of the present invention may be used to reroute flows from some transmission lines but not others, stop flow in one or more transmission lines altogether if, for example, the contaminant level in that line exceeds an acceptable threshold, and redirect flow to improve the timing of delivery or to facilitate storage and transportation requirements.

The foregoing has outlined rather broadly certain aspects of the present invention in order that the detailed description of the invention that follows may better be understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

The present invention is directed to improved methods and systems for, among other things, detecting contaminants in a fluid stream. The configuration and use of the presently preferred embodiments are discussed in detail below. It should be appreciated, however, that the present invention provides many applicable inventive concepts that can be embodied in a wide variety of contexts other than determination of energy content and detection of contaminants in a fluid stream. Accordingly, the specific embodiments discussed are merely illustrative of specific ways to make and use the invention, and do not limit the scope of the invention. In addition, the following terms shall have the associated meaning when used herein:

"fluid infrastructure" means any infrastructure used in connection with the collection, processing, storage, transmission or distribution of a fluid including, without limitation, if the fluid is a hydrocarbon, any infrastructure between the wellhead and the point of retail delivery;

"contaminant" means any undesirable or less desirable chemical within a fluid;

"fluid" means any gas or liquid, including but not limited to a natural gas stream with or without suspended liquids, a natural gas liquids (NGL) stream, or a crude oil stream;

"high resolution" means NIR scans with resolution greater than or equal to 0.01 nanometers;

"high-resolution scanning mode" means scanning at a high resolution over a narrow range of wavelengths;

"low resolution" means NIR scans with resolution in the 0.5 nanometer to 5 nanometer range;

"NIR" and "near infrared" mean the wavelength range between approximately 1350 to 2500 nanometer, or 1.35 to 2.5 micrometer;

"scanning source" means any light source known in the art for scanning the near infrared spectrum, including tunable diode lasers and broadly scanning lasers; and "TDL" means a tunable diode laser, typically used with very narrow beam width at a single set wavelength corresponding to highest absorption of a molecule of interest in a spectroscopic system.

Through use of the embodiments of the present invention, it is possible to determine the composition of the fluid, the energy content of the fluid as well as the quantity of the contaminants of interest in the fluid. Some embodiments of the present invention provide a spectrometer, an optical system and a processing module to determine either or both of the quantity of energy (such as that determined by the hydrocarbon speciation and percentages) and the amount of one or more contaminants in a fluid stream, typically in a fluid infrastructure. These may employ the near infrared band of the electromagnetic spectrum, specifically between the 1300 nm to 2500 nm range. One embodiment focuses on the 1550 nm to 1800 nm range for the carbon hydrogen overtone to resolve the chemicals that contribute energy content to crude oil and natural gas liquids. Other embodiments may utilize 1350 nm to 1800 nm range to identify $CO_2$, $H_2S$ and other chemical components within the spectrum.

Figure 1:
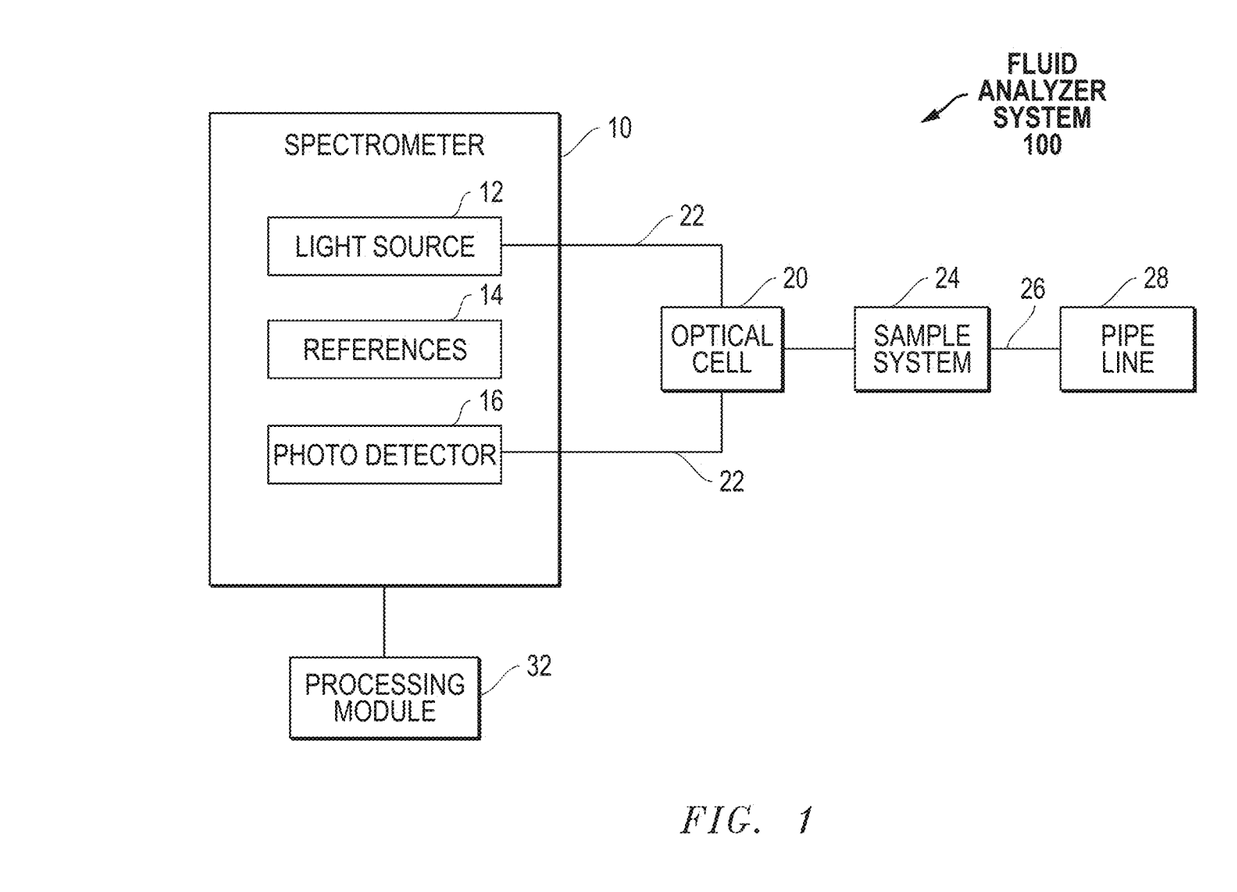
FIG. 1 provides a block diagram of a spectrometer operable to perform spectrographic analysis of fluids in the field.

A representative embodiment of a fluid analyzer system 100 is shown in FIG. 1. A spectrometer 10 known in the art includes a light source 12, integrated wavelength and amplitude references 14, and a photo detector 16. Spectrometer 10 is coupled to an optical cell 20 via fiber optic cables 22. A sample system 24 will extract fluid 26 from a pipe line 28, whether in situ or as a bypass configuration, measure the pressure and temperature of the fluid, direct the fluid through optical cell 20 where it will be exposed to light from the scanning source 12, and reintroduce the sample back into the transmission line 28 or exhaust it to atmosphere. The spectral data will be transmitted back to the photo detector 16 via the fiber optic cables 22. The detector array may, for example, be an Indium Gallium Arsenide (InGaAs) photo detector. The processing module 32 will process the spectrographic data and other measured fluid properties such as temperature and pressure, using various models and computational techniques to determine the chemical composition of the fluid. Other properties of the fluid such as hydrocarbon dew point, specific gravity and compressibility, API gravity, vapor pressure and boiling point may also be computed from the information collected. The results will then be stored for a later transmission and analysis, sent directly to a data gathering location, or both.

The processing module 32 may be a single processing device or a plurality of processing devices. Note that when the processing module 32 implements one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry.

Figure 2:
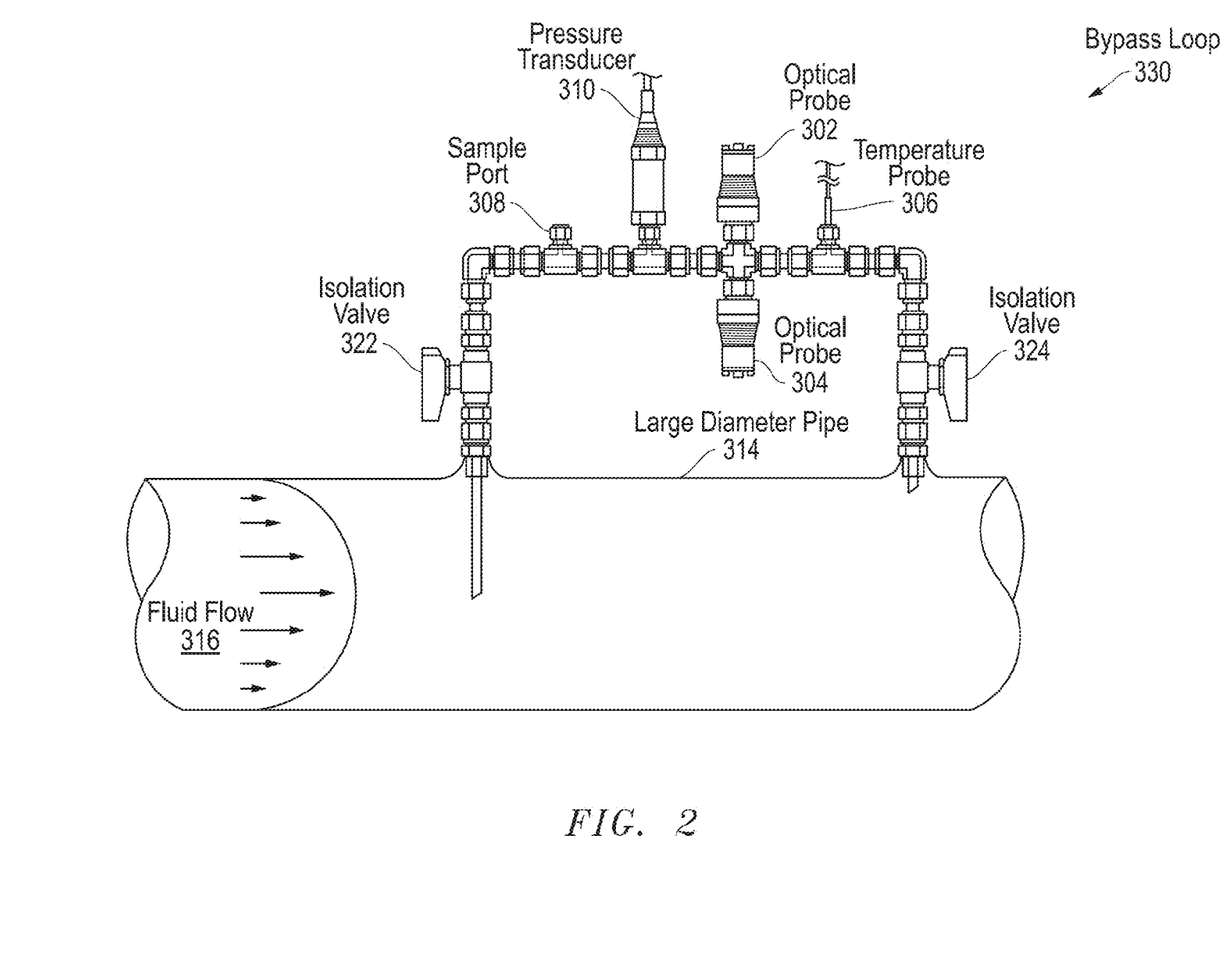
FIG. 2 depicts a system operable to measure the composition of a fluid, including for example crude oil, within a pipeline.

FIG. 2 depicts an application of the foregoing methodology in a fluid measurement system in which individual probes are introduced to a large diameter pipe 314 to measure the chemical composition of a fluid 316 within a pipeline using a bypass loop 330. As depicted here, the sample system 24, optical cell 20, and pipeline 28 of fluid analyzer system 100 would be encompassed in a bypass loop 330. This loop would include isolation valves 322 and 324, optical probes 302 and 304, temperature probe 306, a sample port 308, and a pressure transducer 310. Optical probes 302 and 304 allow spectroscopic measurements to be taken and combined with the results of the pressure transducer 310 and temperature transducer 306 in order to yield information about the quantity of contaminants within the transmission pipe in which the analyzer 100 is installed.

In addition to measuring the energy content of a fluid, it may be useful to measure the quantity of various contaminants in situ. Representative infrared absorption lines for various fluids are given in Table 1. It should be kept in mind that, when reading a given line, consideration must be paid the fundamental line strength as well as to whether the line might overlap with the absorption lines of other fluids that might be present in the sample.

TABLE 1

| Fluid | Formula | Peak Absorption Wavelength (nm) |
| --- | --- | --- |
| Water | H2O | 1392 |
| Ammonia | NH3 | 1512 |
| Carbon Monoxide | CO | 1560 |
| Carbon Monoxide | CO | 1579 |
| Hydrogen Sulfide | H2S | 1579 |
| Methane | CH4 | 1654 |
| Methane | CH4 | 1684 |
| Hydrochloric Acid | HCl | 1730 |
| Nitric Oxide | NO | 1790 |
| Water | H2O | 1800 |
| Water | H2O | 1854 |
| Water | H2O | 1877 |
| Water | H2O | 1826 |
| Nitrous Oxide | N2O | 1960 |
| Carbon Dioxide | CO2 | 2003 |
| Carbon Dioxide | CO2 | 2012 |
| Water | H2O | 2750 |

In one embodiment of the present invention, two or more separate scanning sources are employed and combined with certain data processing techniques and models to provide a real time, in situ measurement of properties of the fluid, such as energy content of the fluid or the amount of a contaminant in the fluid. For example, a first scanning source may scan from a frequency at or lower than the range of interest (i.e. below approximately 1550 nm) up through 1800 nm at a low resolution and a second scanning source, such as a tunable diode laser, concurrently or nearly simultaneously scans at a high resolution across only the narrow wavelength of interest for a contaminant, such as hydrogen sulfide for which the wavelength of interest is approximately 1560-1610 nm. The second scanning source may provide very narrow (e.g. 0.005 nm) step which enables very high resolution over just the wavelength of interest for hydrogen sulfide and may scan at the highest power level possible. The signals obtained from the combined low resolution scan and high resolution scan are used to calculate the energy content of the fluid (expressed in BTUs) based on its chemical composition and the amount of hydrogen sulfide or other contaminant in the fluid.

Figure 3:
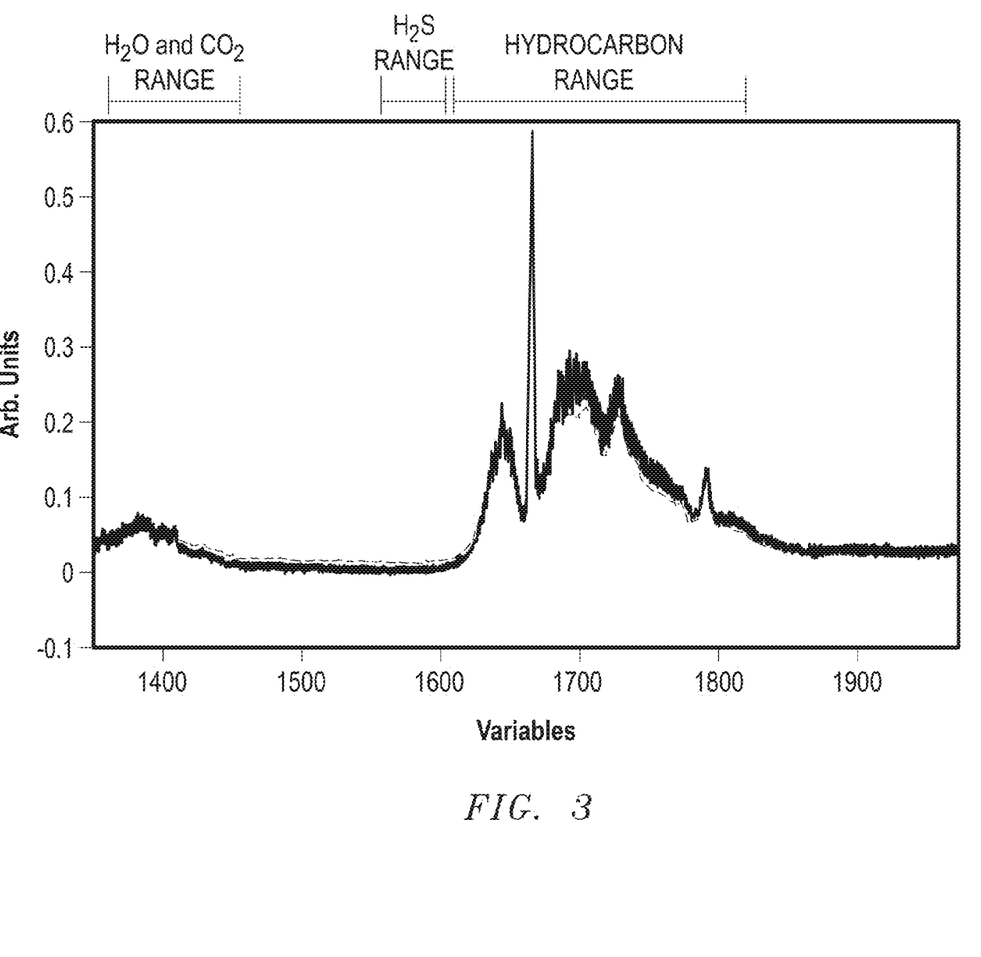
FIG. 3 shows an example of a collected absorption spectra showing absorption versus wavelength between 1350 and 1800 nm.
Figure 4:
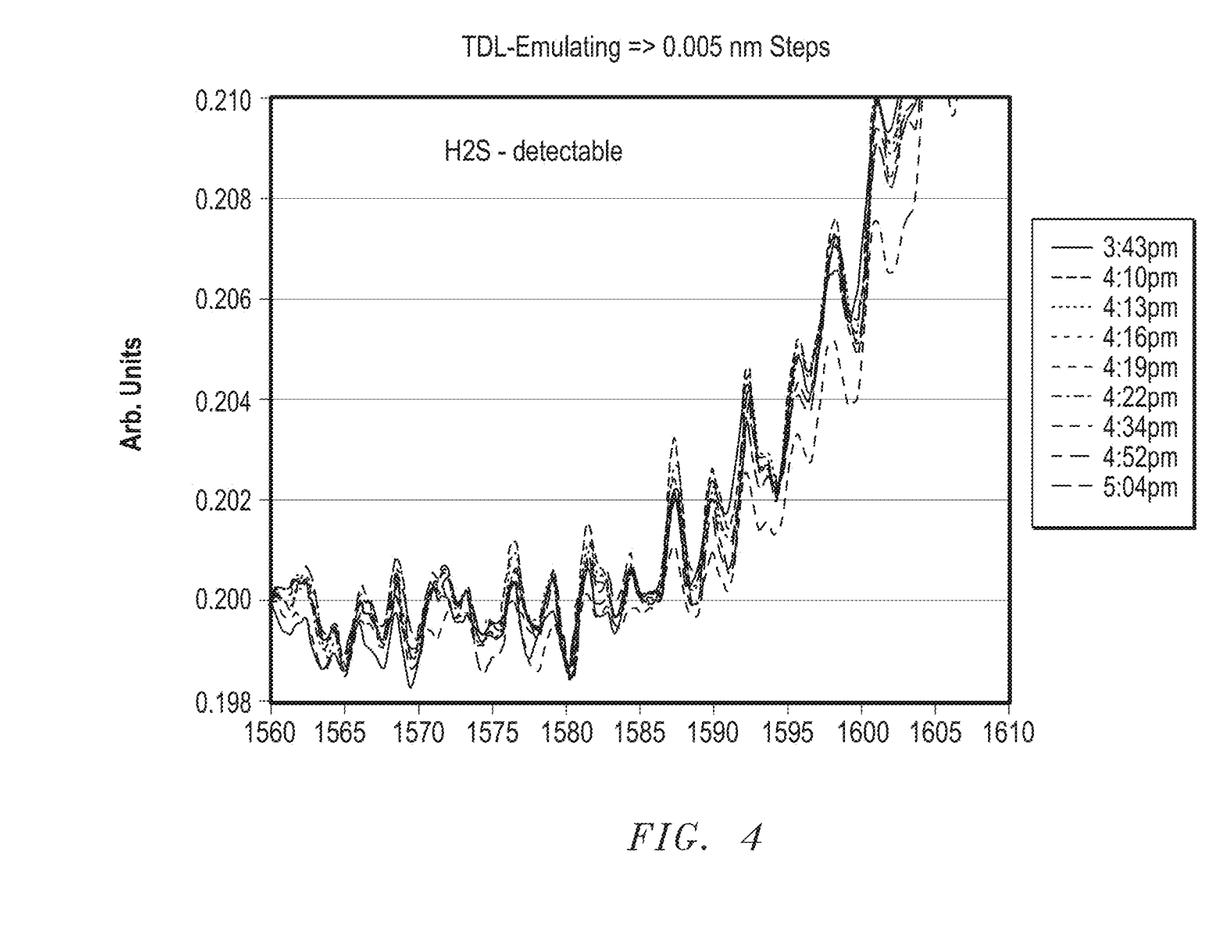
FIG. 4 shows an example of a collected spectrum using one embodiment of the present invention plotting absorption against wavelengths between 1560 nm and 1610 nm.

As one example of the embodiment described above, FIG. 3 shows an absorption spectra between 1350 and 1975 nm resulting from the first scanning source scanning a broad range at low resolution as described above. It is evident that the hydrocarbon range between 1600 and 1800 nm is active, but there is no discernible information in the hydrogen sulfide wavelength range between 1560 and 1610 nm. The hydrogen sulfide wavelength range may be scanned using a second scanning source at a higher resolution, in this case 0.005 nm steps, and the result is shown in FIG. 4. As can be seen in FIG. 4, the smooth appearance of the absorption curve in the hydrogen sulfide range in FIG. 3 is actually a series of peaks and valleys that is not detectable at the lower resolution of the first scanning source.

In another embodiment of the present invention, one scanning source conducts multiple separate scans. The scanning source will first be set to perform a broad scan (e.g. from 1350 to 1800 nm) at a low resolution to determine energy content, and the same scanning source will then scan in high-resolution scanning mode to scan through other smaller regions of interest. The scans may be as narrow as 50 nm and as large as 300 nm. The signals from each scan will be processed through the same above-mentioned processing steps, or alternatively, the extended multiplicative scatter correction and/or other preprocessing steps could be eliminated from the second scan. The processing module 32 could combine the optical data obtained from the multiple scans (one or more high-bandwidth low-resolution and one or more low-bandwidth high-resolution) to determine various properties of the fluid simultaneously, such as energy content and contaminant quantity.

In embodiments of the current invention, scanning sources may scan across specific, narrower range because there are multiple peaks in the contaminant (for example, hydrogen sulfide) region due to the rotational structure of the atom, all of which broaden under pressure. This information can be used to determine, for example, which peaks are free of unwanted interference (e.g., from methane). This allows the processing module to take into account different operating conditions, temperature and pressure, and create and utilize a model that contains a linear regression coefficient and other variables and models that are indicative of the contaminant (e.g., hydrogen sulfide) concentration.

In another embodiment, the first scanning source again scans from a frequency at or lower than approximately 1550 nm up through 1800 nm. However, rather than employing additional scanning sources, software is used to increase the resolution through the contaminant wavelength range. In other words, the signal is processed by increasing the resolution while decreasing the bandwidth of interest. The additional signals (or multiple passes thereof) are then combined with the broad waveband signal to determine the energy content and contaminant content of the fluid stream using the processing module 32 algorithms.

In any embodiment of the current invention, the absorption spectra from both the low resolution scan and the high resolution scans are stored in a database for each set of scans, along with the sample temperature and pressure. Once stored, the collected absorption signals can be standardized and analyzed through post-processing methods. For example, by taking the first derivative of the absorption spectra, the effects of contamination within the fluid infrastructure can be reduced. More specifically, by calculating the change in absorption, rather than absorption itself, it is no longer necessary to know how much spectroscopic light entered the sample, but only how much the transmitted light changed from its average value during the wavelength modulation. In addition, because the change in absorption is not dependent on source intensity, it is not necessary to use a dual beam and a second detector when scanning the fluid.

In some embodiments, the process of converting the raw spectroscopic data via the processing module 32 may then involve dividing the first derivative spectrum by the pressure (in psi) for normalization. One or more calibration models may then be applied to the normalized first derivative spectrum to calculate energy content and contaminant concentrations. It is then possible to employ multivariate empirical modeling methods to develop various calibration models. The models can use one or more of the following elements: (i) principal components analysis (PCA) and partial least squares (PLS) regression to uncover optimal modeling strategies and to detect potential outliers in the calibration data set; (ii) if any sample or spectral variables are detected in the calibration data, exclude them from being used to build the models; (iii) use of partial least squares (PLS) regression to construct predictive calibration models from the calibration data generating a series of regression coefficients which, when multiplied with the absorbance values of an unknown fluid sample's spectrum, yield the property of interest; (iv) use of genetic algorithms (GA) to select subsets of the spectral response variables to use in the predictive models to make the PLS models more robust with respect to known interfering effects in the spectra; and/or (v) use of PCA to generate an "outlier model" which can be run on-line to assess whether a field-collected spectrum is abnormal with respect to the spectra that were used to develop the models.

Crude oil is typically pumped from the wellhead into gathering lines to a point where it enters a common carrier pipeline and eventually arrives at the refinery. The present invention contemplates that the fluid analyzer systems of the present invention would be placed at transfer points between the wellhead and the refinery, such as when custody of the oil is transferred from a flow line to a gathering line or from a gathering line to a common carrier line or from a carrier line into the refinery. By positioning the fluid analyzer systems in locations along the pipeline, it is possible to determine the energy value and contaminant level of the oil in real time, thereby allowing the flow among various points to be altered, thereby altering the composition of the oil arriving at the refinery.

Figure 5:
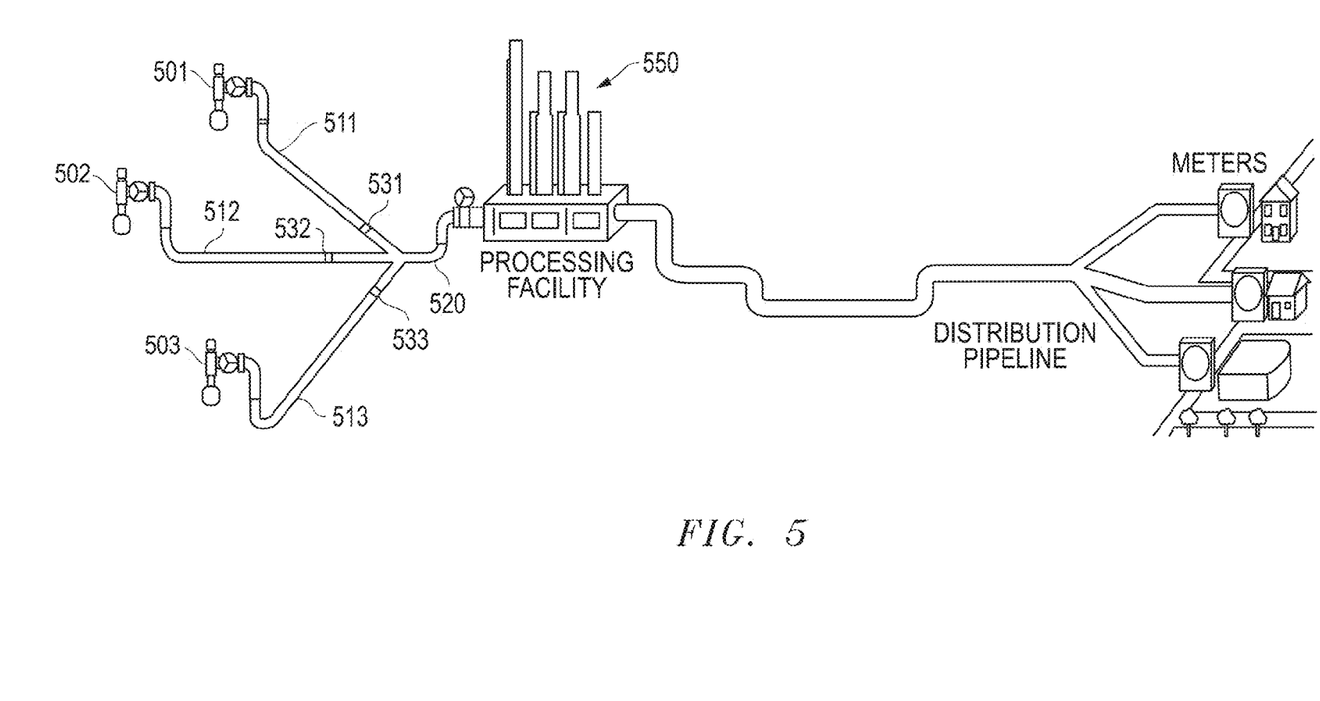
FIG. 5 depicts an oil transmission and processing system that would beneficially utilize embodiments of the present invention.

Referring now to FIG. 5, which depicts transmission pipelines 511, 512 and 513 used to transport oil from wellheads 501, 502 and 503 to a downstream line 520 and on to the refinery 550. The energy content and specific hydrocarbon speciation of oil flowing from wellhead 501 may be different than the energy content and speciation of the oil flowing from wellhead 502. Similarly, the type or amount of contaminants in oil flowing from wellhead 501 may be different than those in the oil flowing from wellhead 502 or 503. Inasmuch as oil or gas are bought and sold based on energy content and/or the speciation of that hydrocarbon, it is often necessary or desirable to determine the makeup of the product in situ in real time.

In various embodiments of the present invention, fluid analyzers 531, 532 and 532 are located along transmission line 511, 512 and 513 respectively. In general, the sample system and optical cell of the fluid analyzer system would be encompassed in a bypass loop which would typically isolation valves, optical probes, temperature probe, a sample port, and a pressure transducer. As discussed earlier above, the fluid analyzer could provide real-time information about the energy content and speciation of the fluid in the gathering line which could permit each line to be throttled as necessary to create the desired output. The information may be used to make various businesses, maintenance, and processing decisions based on the real-time feed or historically trended data from the instruments.

There are numerous reasons why it may be advantageous to monitor and adjust the relative flows of a fluid in the transmission lines in real time. For example, significant interest, especially at custody transfer points, exists in the ability to have a quick and accurate measurement of energy content, hydrocarbon speciation and contaminant level. These installations will lead to a much more efficient and accurate market place. In addition, the information may be used to reroute flows from some transmission lines but not others, stop flow in one or more transmission lines altogether if the contaminant level exceeds an acceptable threshold, redirecting flow to improve the timing of the delivery or to facilitate storage and transportation requirements.

It would also be useful to know the constituent compositions of the oil entering the common carrier line from each transmission line in real time so that the composition of the oil in the common carrier line can be monitored, blended with other streams, and adjusted as desired to meet individual refinery specifications. It would also allow for arbitrage of very specific oil compositions to take place even upstream or midstream, well before selling to the refineries. In addition, it would allow the refineries to significantly increase their production efficiency and thus profit margins by monitoring incoming oil composition and paying more or less for specific blends, rather than just relying on API gravity numbers.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise. The term "connected" means "communicatively connected" unless otherwise defined.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of methods for determining the amount of contaminants present in a fluid known in the art, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

What is claimed is:

1. A method of blending fluids, comprising:
    transmitting a first fluid through a first optical cell operable within a first transmission line into a downstream line;
    transmitting a second fluid through a second optical cell operable within a second transmission line into said downstream line;
    scanning said first fluid over a broad wavelength range within the near infrared spectrum using a first tunable laser within said first optical cell to determine a property of said first fluid using spectrographic analysis from said first tunable laser;
    scanning said second fluid over a broad wavelength range within the near infrared spectrum using a second tunable laser within said second optical cell to determine a property of said second fluid using spectrographic analysis from said second tunable laser;
    determining a property of said first fluid using chemometric analysis of said spectrographic analysis from said first tunable laser and determining a property of said second fluid using chemometric analysis of said spectrographic analysis from said second tunable laser; and
    altering said transmission of said first fluid through said first transmission line or said second fluid through said second transmission line based on said property of said first fluid and said property of said second fluid, thereby altering a property of a fluid in said downstream line.

2. The method of claim 1, wherein said first fluid and said second fluid are hydrocarbons.

3. The method of claim 1, wherein said tunable laser scans a wavelength range from about 1350 nm to about 1850 nm at high resolution.

4. A system for blending fluids in transmission lines, comprising:
a first optical cell operable within a first transmission line, wherein a first fluid is transmitted through said first transmission line into a downstream line;
a second optical cell operable within a second transmission line, wherein a second fluid is transmitted through said second transmission line into said downstream line;
a first tunable laser configured to scan said first fluid in said first transmission line over a broad wavelength range within the near infrared spectrum;
a second tunable laser configured to scan said second fluid in said second transmission line over a broad wavelength range within the near infrared spectrum;
a central processing unit configured to evaluate said scan from said first tunable laser to determine a property of said first fluid and to evaluate said scan from said second tunable laser to determine a property of said second fluid;
a control mechanism configured to alter said transmission of said first fluid through said first transmission line or said transmission of said second fluid through said second transmission line based on said property of said first fluid and said property of said second fluid, thereby altering a property of a fluid in said downstream line.

5. The system of claim 4, wherein said first fluid and said second fluid are hydrocarbons.

6. The system of claim 4, wherein said property is energy content.

7. The system of claim 4, wherein said property is compositional makeup.

8. The system of claim 4, wherein said property is a physical property.

9. The system of claim 4, wherein said tunable laser scans the wavelength range from about 1350 nm to about 1850 nm at high resolution.

10. A method of blending crude oil, comprising:
transmitting a first crude oil through a first optical cell operable within a first transmission line into a downstream line;
transmitting a second crude oil through a second optical cell operable within a second transmission line into said downstream line;
scanning said first crude oil over a broad wavelength range within the near infrared spectrum using a first-tunable laser within said first optical cell to determine a property of said first crude oil using spectrographic analysis from said first tunable laser;
scanning said second crude oil over a broad wavelength range within the near infrared spectrum using a second-tunable laser within said second optical cell to determine a property of said second crude oil using spectrographic analysis from said second tunable laser;
determining a property of said first crude oil using chemometric analysis of said spectrographic analysis from said first tunable laser and determining a property of said second crude oil using chemometric analysis of said spectrographic analysis from said second tunable laser; and
altering said transmission of said first crude oil through said first transmission line or said second crude oil through said second transmission line based on said property of said first crude oil and said property of said second crude oil, thereby altering a property of a crude oil in said downstream line.

11. The method of claim 10, wherein said property is energy content.

12. The method of claim 10, wherein said property is compositional makeup.

13. The method of claim 10, wherein said property is a physical property.

14. The method of claim 10, wherein said tunable laser scans the wavelength range from about 1350 nm to about 1850 nm at high resolution.

15. A method of blending fluids, comprising:
transmitting a first fluid through a first optical cell operable within a first transmission line into a downstream line;
transmitting a second fluid through a second optical cell operable within a second transmission line into said downstream line;
scanning said first fluid over a broad wavelength range within the near infrared spectrum using a first-tunable laser within said first optical cell to determine a property of said first fluid using spectrographic analysis from said first tunable laser;
scanning said first fluid over a narrow wavelength range within the near infrared spectrum using said first tunable laser;
scanning said second fluid over a broad wavelength range within the near infrared spectrum using a second-tunable laser within said second optical cell to determine a property of said second fluid using spectrographic analysis from said second tunable laser;
determining a property of said first fluid using chemometric analysis of said spectrographic analysis, and determining quantity of a contaminant in said fluid using said spectrographic analysis, from said first tunable laser and determining property of said second fluid using chemometric analysis of said spectrographic analysis from said second tunable laser; and
altering said transmission of said first fluid through said first transmission line or said second fluid through said second transmission line based on said property and said quantity of said contaminant of said first fluid and said property of said second fluid, thereby altering a property of a fluid in said downstream line.

16. The method of claim 15, wherein said property is energy content.

17. The method of claim 15, wherein said property is compositional makeup.

18. The method of claim 15, wherein said property is a physical property.

19. The method of claim 15, wherein said first tunable laser scans said broad wavelength range and said narrow wavelength range concurrently.

20. The method of claim 15, wherein said first tunable laser scans said broad wavelength range and said narrow wavelength range sequentially.

21. The method of claim 15, wherein said fluid is crude oil.

22. The method of claim 15, wherein said broad wavelength range is between about 1350 nm and about 2500 nm.

23. The method of claim 15, wherein said narrow wavelength range is between about 1560 nm and about 1610 nm.

24. The method of claim 15, wherein said contaminant is hydrogen sulfide.

* * * * *